United States Patent [19]

Schlüssler et al.

[11] 4,444,756

[45] Apr. 24, 1984

[54] IODINE CONTAINING DISINFECTANTS

[75] Inventors: Hans-Joachim Schlüssler, Haan; Ferdinand Koch, Hilden, both of Fed. Rep. of Germany

[73] Assignee: Henkel KGaA, Duesseldorf, Fed. Rep. of Germany

[21] Appl. No.: 374,342

[22] Filed: May 3, 1982

[30] Foreign Application Priority Data

Sep. 19, 1981 [DE] Fed. Rep. of Germany ....... 3137339

[51] Int. Cl.$^3$ ..................... A61L 13/00; A61K 33/18
[52] U.S. Cl. ..................... 424/150; 252/106
[58] Field of Search ............. 252/106; 424/150; 134/22.13, 22.16

[56] References Cited

U.S. PATENT DOCUMENTS

| | | | |
|---|---|---|---|
| 2,943,014 | 6/1960 | Loonam | 424/150 |
| 2,977,315 | 3/1961 | Scheib et al. | 252/106 |
| 3,150,096 | 9/1964 | Schmidt et al. | 252/106 |
| 3,220,951 | 11/1965 | Cantor et al. | 252/106 |
| 3,274,116 | 9/1966 | Mills | 252/106 |
| 3,308,014 | 3/1967 | Cantor et al. | 424/150 |
| 3,984,341 | 10/1976 | Haschke et al. | 252/106 |
| 4,081,396 | 3/1978 | Batterson | 252/106 |
| 4,151,275 | 4/1979 | Cantor et al. | 424/80 |
| 4,271,149 | 6/1981 | Winicov et al. | 424/150 |

FOREIGN PATENT DOCUMENTS 2527795 12/1976 Fed. Rep. of Germany.

*Primary Examiner*—P. E. Willis, Jr.
*Attorney, Agent, or Firm*—Ernest G. Szoke; Henry E. Millson, Jr.

[57] ABSTRACT

Aqueous disinfectant concentrates and solutions containing iodine, potassium or sodium iodide, and orthophosphoric acid in controlled quantities, including, optionally, a phosphonic acid with complexing properties. Also, a method of disinfecting a surface comprising applying to such surface a solution of the invention.

14 Claims, No Drawings

IODINE CONTAINING DISINFECTANTS

BACKGROUND OF THE INVENTION

The use of iodine containing disinfectants containing potassium or sodium iodide and elemental iodine in an aqueous phase for medicinal purposes is well known in the art (e.g. tincture of iodine). In addition to the above ingredients, such disinfectants sometimes contain calcium iodide as well as varying amounts of solubilizing intermediates such as ethanol, isopropanol, or glycerine.

During the past few years, iodine products containing surface active anionic, cationic, and preferably, non-ionic substances have been introduced to the marketplace under the general designation of iodophors. These products are used not only in medicine, but also in the food industry. This group of iodophors contains, in addition to the above mentioned surface active substances and elemental iodine and iodides, varying amounts of phosphoric acid.

Additionally, the surface active substances are sometimes replaced partially or completely by high polymer substances such as for instance polyacrylates or other substituted polycarboxylic acids. Such produces may also contain various amounts of solubilizing intermediaries such as isopropanol or ethanol.

It has been shown that the aqueous or alcohol containing solutions which are used as pharmaceutical products give unfavorable results when used for disinfecting solid surfaces which are to come into contact with foodstuffs after disinfection and rinsing. Additionally, some surfaces (e.g. composed of synthetic materials) have shown brownish discolorations after treatment. Also, the stability of the disinfecting solutions has been insufficient, which is noticable from lightening of the characteristic brownish-yellow color of the elemental iodine in the aqueous phase.

The group of iodophors, on the other hand, do exhibit good bacteriological activity when used to disinfect solid surfaces. However, certain disadvantages have become evident in their application. For instance, even when foam inhibitors are used, foam-free operation is not possible when the iodophors are used in equipment designed for processing various foodstuffs. Additionally, such preparations pollute waste water with their surface active as well as non-surface active polymeric compounds, e.g. by elevating the so-called COD values (chemical-oxygen demand). It has also been shown that the rinsability of iodophors is not as good as that of substances which are free of surface active agents. Additionally, stress corrosion caused by nonionic, ethoxylated and/or propoxylated block polymers, which serve as the iodine carriers, have been observed in acrylic glass used in milking machine pipes.

Another disadvantage of the iodophors is the fact that the dissolving intermediaries, such as for instance ethyl alcohol and isopropyl alcohol, not only pollute the waste water, but also require special safety precautions during manufacture (explosion-proof installations) and during packaging (degassing vents) due to their relatively low flash point. Examples of references disclosing prior art iodine-containing compositions of the type discussed above are given below:

West German Pat. No. DT 25 27 795 B2 discloses aqueous compositions containing from 0.5 to 3 percent by weight of iodine, from 10 to 30 percent by weight phosphoric acid, from 5 to 30 percent by weight of acetic acid, and from 0.5 to 20 percent by weight of a polymer having a molecular weight between 500 and 10,000 of the formula

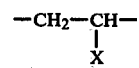

where X is 65-90% —COOH and 10-35%

U.S. Pat. No. 3,220,951 to Cantor et al discloses detergent iodine compositions containing iodine, a water soluble ethoxylated nonionic surface active agent/detergent as a carrier for the iodine and an acid which is hydroxyacetic acid, either alone or in admixture with phosphoric acid.

DETAILED DESCRIPTION OF THE INVENTION

It has now been found that the disadvantages and shortcomings of prior art can be avoided by using the iodine containing disinfectant concentrates and solutions of the present invention.

The aqueous concentrates of the invention, which are diluted with water to form disinfectant solutions for disinfecting surfaces of equipment, pipes and the like which come into contact with foodstuffs, contain the following ingredients:

(a) from about 0.1 to about 3% by weight, preferably about 1 to about 2% by weight, of $I_2$, (b) from about 0.2 to about 6% by weight, preferably about 2 to about 4% by weight of potassium iodide or sodium iodide (or a mixture thereof), and (c) from about 1 to about 15% by weight of orthophosphoric acid, with the remainder water, preferably distilled or deionized water.

Also, there can optionally be present up to about 3% and generally from about 0.1 to about 3% by weight, preferably from about 1 to about 2% by weight of a phosphonic acid that exhibits complex forming properties with calcium ions. The following are examples of phosphonic acids that will form complexes with calcium ions: 1-hydroxyalkane-1,1-diphosphonic acids, such as 1-hydroxyethane-1,1-diphosphonic acid; 1-aminoalkane-1,1-diphosphonic acids such as 1-aminoethane-1,1-diphosphonic acid; nitrilotrimethylene phosphonic acid; and preferably, aminotrimethylene phosphonic acid.

The aqueous disinfectant solutions of the invention, which are useful for disinfecting the surfaces of equipment, pipes, and other materials having solid surfaces that come into contact with foodstuffs, and which are applied to such surfaces by known procedures, are formed by adding a desired quantity of one of the above concentrates to water. The aqueous disinfectant solutions of the invention contain from about 0.1 to about 10% by weight, preferably about 0.5 to about 2% by weight, of a concentrate of the invention. Of course, these solutions can also be used to disinfect other solid surfaces as well, such as for example floors of hospitals and other compatible solid surfaces where disinfection is desired.

The concentrates and disinfectant solutions of the invention have many advantages over prior art compositions. First of all, the concentrates and solutions of the invention do not contain any wetting agents, iodophors, or non-surface active polymer compounds, with the attendant disadvantages of such ingredients which are discussed above. They are also free of dissolving intermediaries such as monovalent or bivalent alcohols. Furthermore, the concentrates remain stable after a one year storage, and do not exhibit a decrease in active iodine content. No precipitation of elementary iodine is observed inside the storage containers. Additionally, there are no differences in the bacteriological results with the present solutions as compared to results obtained with typical iodophors. Moreover, the claimed mixtures can be manufactured more economically than can prior art compositions.

The present invention can be more fully appreciated from the following examples, which are given for illustration purposes only, and not to limit the invention. In the following examples all percentages are percentages by weight unless otherwise indicated.

EXAMPLE I

Two concentrates were prepared, Concentrate A which is a concentrate prepared in accordance with the teachings of the prior art, and Concentrate B which is a concentrate prepared in accordance with the present invention. These concentrates were prepared by mixing together the ingredients given below in the concentrations shown below.

| Concentrate A (prior art product) | |
|---|---|
| % | Ingredient |
| 2 | $I_2$ |
| 4 | $K_I$ |
| 5 | nonylphenol-ethylene oxide (9 moles)-propylene oxide (10 moles) |
| 50 | phosphoric acid |
| 10 | isopropanol |
| 29 | distilled water |

| Concentrate B (present invention) | |
|---|---|
| % | Ingredient |
| 2 | $I_2$ |
| 4 | $K_I$ |
| 10 | phosphoric acid |
| 84 | distilled water |

Concentrate A and Concentrate B were each diluted with water to give 1% solutions (Solution A and Solution B respectively). Solution A was then used to disinfect a fermentation tank which had previously been cleaned and rinsed with water. Solution A foamed excessively and required a time consuming final rinse. When Solution B was used to disinfect the same fermentation tank, no foaming took place and the solution was readily rinsed off with a significantly smaller quantity of water compared to that required for Solution A.

EXAMPLE II

Concentrate A and Concentrate B, prepared as in EXAMPLE I, were each diluted with water to give 0.5% solutions (Solution A and Solution B respectively). Solution A was then used to disinfect acrylic glass milking machine pipes for a period of approximately three weeks. At the end of this period, the acrylic glass pipe sections exhibited characteristic stress corrosion. After the damaged pipe sections were replaced with uncorroded sections, Solution B was then used to disinfect the acrylic glass pipes for a period of approximately three weeks. At the end of this period, the pipes were examined, and all were free of stress corrosion.

EXAMPLE III

Concentrate A and Concentrate B, prepared as in EXAMPLE I, were tested for storage stability in conventional low pressure polyethylene containers placed together under constant temperature conditions. After a storage period of three months, the containers filled with Concentrate A exhibited a characteristic absorption phenomenon which made stacking of the containers on regular shipping pallets impossible. The containers filled with Concentrate B did not exhibit this undesirable effect.

EXAMPLE IV

Two concentrates were prepared, Concentrate C which is a concentrate prepared in accordance with the teachings of the prior art, and Concentrate D which is a concentrate prepared in accordance with the present invention. These concentrates were prepared by mixing together the ingredients shown below in the concentrations shown below.

| Concentrate C (prior art concentrate) | |
|---|---|
| % | Ingredient |
| 1 | $I_2$ |
| 2 | NaI |
| 6 | polyacrylic acid |
| 60 | phosphoric acid |
| 15 | ethyl alcohol |
| 16 | distilled water |

| Concentrate D (present invention) | |
|---|---|
| % | Ingredient |
| 1 | $I_2$ |
| 2 | NaI |
| 12 | phosphoric acid |
| 1 | nitrilotrimethylene phosphonic acid |
| 84 | distilled water |

Concentrate C and Concentrate D were each diluted with water to give 1.5% solutions (Solution C and Solution C respectively).

Solution C was then used in a dairy to disinfect milk tanks and pipe lines, following their cleaning and rinsing. Solution C was used for three days, after which the solution, which had minute amounts of soil in it, was found to have a COD value (chemical oxygen demand in mg/l) of 2,400 mg/l of $O_2$. Solution C was then drained into the sewer system.

The same milk tanks and pipe lines (which were cleaned and rinsed as above prior to the use of Solution C) were then disinfected with Solution D, which was used in the same manner as Solution C for three days. After three days' use, Solution D had a COD value of only 1,200 mg/l of $O_2$.

What is claimed is:

1. An aqueous concentrate, useful in the preparation of disinfecting solutions, consisting essentially of
   (a) from about 0.1 to about 3% by weight of $I_2$;
   (b) from about 0.2 to about 6% by weight of either
      (i) potassium iodide, (ii) sodium iodide, or
      (iii) a mixture of potassium iodide and sodium iodide;
   (c) from about 1 to about 15% by weight of phosphoric acid; and
   (d) from about 0.1 to about 3% by weight of a phosphonic acid having the ability to complex calcium ions.

2. A concentrate in accordance with claim 1 wherein the range of iodide in (b) is from about 2 to about 4% by weight.

3. A concentrate in accordance with claim 1 wherein the range of $I_2$ in (a) is from about 1 to about 2% by weight.

4. A concentrate in accordance with claim 1, 2, or 3 wherein in (d) from about 1 to about 2% by weight of a phosphonic acid having the ability to complex calcium ions is present.

5. An aqueous disinfectant solution comprising from about 0.1 to about 10% by weight of a concentrate consisting essentially of:
   (a) from about 0.1 to about 3% by weight of $I_2$;
   (b) from about 0.2 to about 6% by weight of either
      (i) potassium iodide, (ii) sodium iodide, or
      (iii) a mixture of potassium iodide and sodium iodide;
   (c) from about 1 to about 15% by weight of phosphoric acid; and
   (d) from about 0.1 to about 3% by weight of a phosphonic acid having the ability to complex calcium ions.

6. A solution in accordance with claim 5 in which from about 0.5 to about 2% by weight of said concentrate is present in the solution.

7. A solution in accordance with claim 5 wherein the range of iodide in (b) in the concentrate is from about 2 to about 4% by weight.

8. A solution in accordance with claim 5 wherein the range of $I_2$ in (a) in the concentrate is from about 1 to about 2% by weight.

9. A solution in accordance with claim 5, 6, 7, or 8 wherein in (d) from about 1 to about 2% by weight of a phosphonic acid having the ability to complex calcium ions is present.

10. A process for disinfecting a surface comprising contacting said surface with an aqueous disinfectant solution containing from about 0.1 to about 10% by weight of a concentrate consisting essentially of:
    (a) from about 0.1 to about 3% by weight of $I_2$;
    (b) from about 0.2 to about 6% by weight of either
       (i) potassium iodide, (ii) sodium iodide, or
       (iii) a mixture of potassium iodide and sodium iodide;
    (c) from about 1 to about 15% by weight of phosphoric acid; and
    (d) from about 0.1 to about 3% by weight of a phosphonic acid having the ability to complex calcium ions.

11. A process in accordance with claim 10 in which from about 0.5 to about 2% by weight of said concentrate is present in the disinfectant solution.

12. A process in accordance with claim 10 wherein the range of iodide in (b) in the concentrate is from about 2 to about 4% by weight.

13. A process in accordance with claim 10 wherein the range of $I_2$ in (a) in the concentrate is from about 1 to about 2% by weight.

14. A process in accordance with claim 10, 11, 12 or 13 wherein in (d) from about 1 to about 2% by weight of a phosphonic acid having the ability to complex calcium ions is present.

* * * * *